United States Patent [19]

Ho et al.

[11] 4,359,586

[45] Nov. 16, 1982

[54] SYNTHESIS 2-ALKYL CYCLOPENTENOLONES

[75] Inventors: Tse-Lok Ho, Jacksonville; Shing-Hou Liu, Atlantic Beach, both of Fla.

[73] Assignee: SCM Corporation, New York, N.Y.

[21] Appl. No.: 233,630

[22] Filed: Feb. 12, 1981

[51] Int. Cl.³ .................... C07C 45/58; C07C 17/30
[52] U.S. Cl. .................... 568/341; 568/364; 570/214; 570/215; 549/531
[58] Field of Search .............. 570/186, 214, 215, 236; 568/364, 341; 260/348.29, 248.31

[56] References Cited

U.S. PATENT DOCUMENTS

| | | | |
|---|---|---|---|
| 2,833,787 | 5/1958 | Carlson et al. | 260/348.31 |
| 2,951,878 | 9/1960 | Neureiter | 570/214 |
| 2,981,756 | 4/1961 | Neureiter | 570/214 |
| 3,326,842 | 6/1967 | Ketley | 570/214 |
| 3,462,453 | 8/1969 | Popoff et al. | 570/214 |
| 3,657,348 | 4/1972 | Tobey | 568/364 |
| 4,012,430 | 3/1977 | Verbrugge et al. | 570/214 |

OTHER PUBLICATIONS

Keller, "Compendium of Phase Transfer Reactions," (1978).
Ketley et al., J. Org. Chem., vol. 31, pp.305–308, (1966).

*Primary Examiner*—James H. Reamer
*Attorney, Agent, or Firm*—A. Joseph Gibbons

[57] ABSTRACT

2-Hydroxy-3-methylcyclopent-2-en-1-one was synthesized in a five-step synthesis starting from 2-methyl-1,3-butadiene. Novel intermediate steps include the hot tube isomerization of 1,1-dihalo-2-methyl-2-vinylcyclopropane to give 1-methyl-4,4-dihalocyclopent-1-ene, hydrolysis to 3-methyl-2-cyclopenten-1-one, epoxidation of the latter using a phase transfer catalyst, followed by catalyzed isomerization to produce 2-hydroxy-3-methylcyclopent-2-en-1-one in high overall yield.

9 Claims, 2 Drawing Figures

FIG. 1 GAS CHROMATOGRAM
2,3-EPOXY-3-METHYLCYCLOPENTANONE 2,3-EPOXY-3-METHYLCYCLOPENTANONE

SYNTHESIS 2-ALKYL CYCLOPENTENOLONES

BACKGROUND OF THE INVENTION

The invention relates to a new synthesis of 3-alkyl-2-cyclopenten-2-ol-1-ones and particularly 3-methyl-2-cyclopenten-2-ol-1-one. The latter compound has been found among the thermal decomposition products of wood, maple syrup, and roasted coffee. Owing to the distinguished organoleptic properties, this compound and its alkyl homologs have enjoyed widespread use as food flavors. The limited availability of these compounds from natural sources has spurred synthetic efforts which have resulted in numerous publications and patents related to the synthesis of methylcyclopentenolone.

BRIEF SUMMARY OF THE INVENTION

Although many syntheses of 3-methyl-2-cyclopenten-2-ol-1-one are reported in the literature, there is a strong need for an improved and more straightforward synthesis of these compound types. Resolution of the problem has been achieved by the instant five-step synthesis. These compounds are also sometimes referred to and named as 2-hydroxy-3-methylcyclopent-2-en-1-one.

One aspect of the present invention includes a process for the preparation of cyclopentenolones having the structure

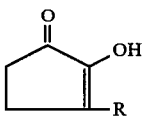

wherein R is a $C_{1-4}$ straight or branched chain lower alkyl radical which comprises:

(a) reacting a 2-alkyl substituted butadiene in a two-phase system with dihalocarbene to produce a 1,1-dihalo-2-alkyl-2-vinylcyclopropane.

(b) passing the product of reaction (a) through a hot tube reactor at about 200°–350° C. and recycling the throughput products until substantially all of the starting product is isomerized to 1-alkyl-4,4-dihalocyclopent-1-ene.

(c) hydrolyzing 1-alkyl-4,4-dihalocyclopent-1-ene under acid catalyst conditions to produce a 3-alkyl-2-cyclopenten-1-one.

(d) epoxidizing the product of reaction (c) to form 2,3-epoxy-3-alkylcyclopentanone.

(e) isomerizing said 2,3-epoxy-3-alkylcyclopentanone under acid catalysis and isolating 2-hydroxy-3-alkylcyclopent-2-en-1-one.

Another aspect relates to the preparation of 2-hydroxy-3-methylcyclopent-2-en-1-one comprising:

(a) reacting 2-methylbutadiene in a two-phase system with a dichlorocarbenoid species in the presence of a catalytic amount of quaternary ammonium salt; and isolating 1,1-dichloro-2-methyl-2-vinylcyclopropane.

(b) passing the product of reaction (a) in an insert carrier through a hot tube reactor and heated from about 200° C. to about 300° C. and recycling the product until substantially all of the 1,1-dichloro-2-methyl-2-vinylcyclopropane has been converted to 1-methyl-4,4-dichlorocyclopent-1-ene.

(c) hydrolyzing 1-methyl-4,4-dichlorocyclopent-1-ene at the temperatures from about 40°–100° C. in the presence of a catalyst selected from the group consisting of acid catalyst, base catalyst or aqueous metal ion catalyst and isolating 3-methyl-2-cyclopenten-1-one therefrom.

(d) epoxidizing said 3-methyl-2-cyclopenten-1-one by reacting with peroxide in a two-phase system containing a phase transfer catalyst to form 2,3-epoxy-3-methylcyclopentanone.

(e) isomerizing said 2,3-epoxy-3-methylcyclopentanone under acid catalysis and isolating 2-hydroxy-3-methylcyclopent-2-en-1-one.

Yet another aspect includes a process for the preparation 1-methyl-4,4-dichlorocyclopent-1-ene which comprises (a) reacting in a two-phase system 1 to 4 moles isoprene with dichlorocarbene in the presence of a catalytic amount of an amine quaternary salt to produce 1,1-dichloro-2-methyl-2-vinylcyclopropane; (b) passing said vinylcyclopropane in an inert gas sequentially through a hot tube at from about 200° C. to 350° C. to isomerize to 1-methyl-4,4-dichlorocyclopent-1-ene.

Yet a further aspect relates to a process for the conversion of 1-methyl-4,4-dihalocyclopent-1-ene to 2-hydroxy-3-methylcyclopent-2-en-1-one which comprises hydrolyzing 1-methyl-4,4-dihalocyclopent-1-ene in the presence of a catalyst selected from the group consisting of acid catalyst, basic catalyst and/or aqueous metal ion catalyst at temperatures of about 40° C. to 100° C. and isolating 3-methyl-2-cyclopenten-1-one therefrom; epoxidizing said 3-methyl-2-cyclopenten-1-one by reacting with basic hydrogen peroxide, in a two-phase system containing a phase transfer catalyst; isolating said 2,3-epoxy-3-methylcyclopentan-1-one and isomerizing it to 2-hydroxy-3-methylcyclopent-2-en-1-one.

Another important aspect of the present invention relates to total synthesis starting from a 2-alkylbutadiene of 2-hydroxy-3-methylcyclopent-2-en-1-one and related 3-alkyl analogs by the combination of the various aforesaid steps and those specifically illustrated in the best mode examples.

DETAILED DESCRIPTION OF THE INVENTION

Figure 1:
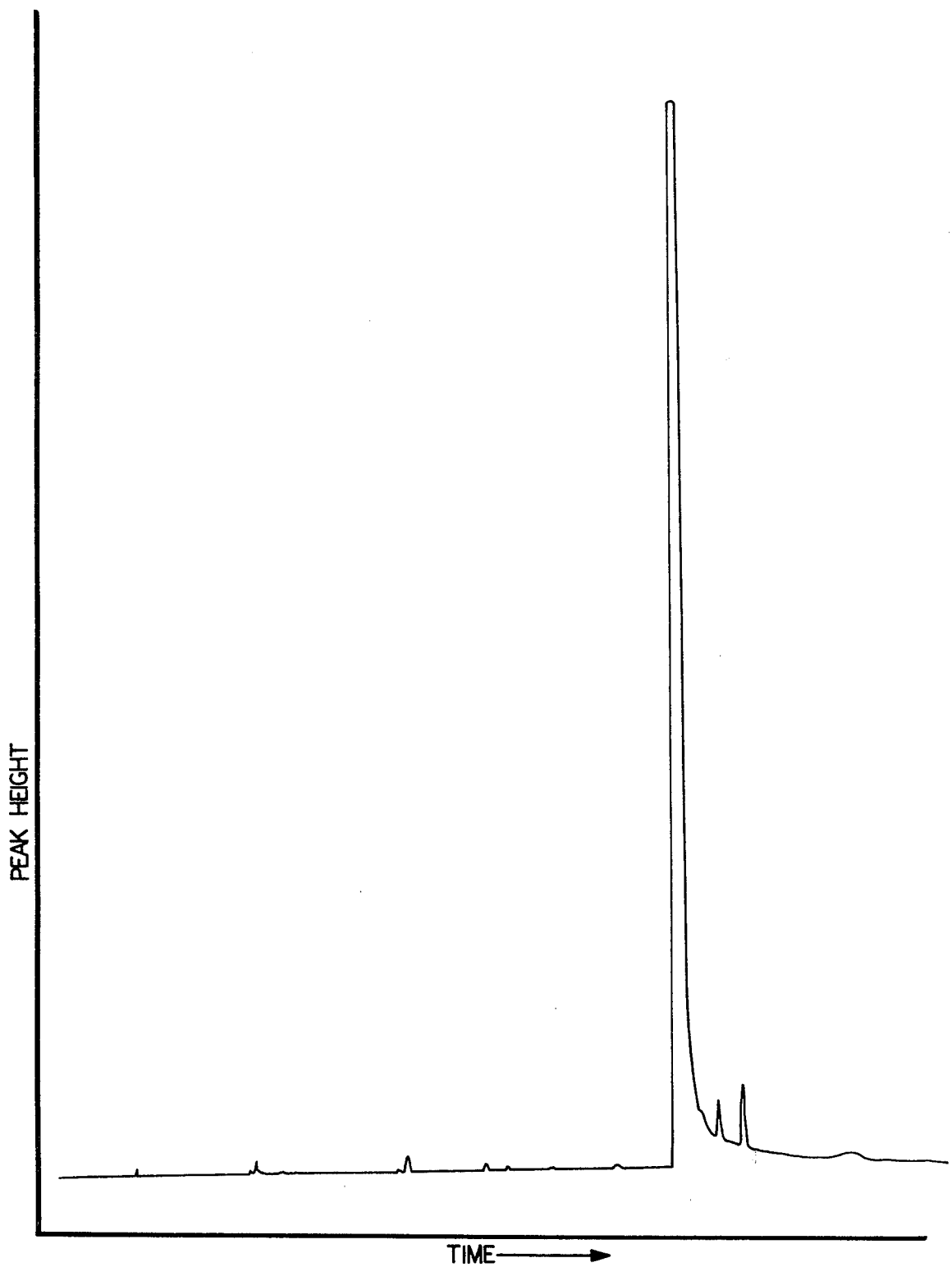

The total synthesis of 2-hydroxy-3-methylcyclopent-2-en-1-one from isoprene is best illustrated with respect to the following scheme.

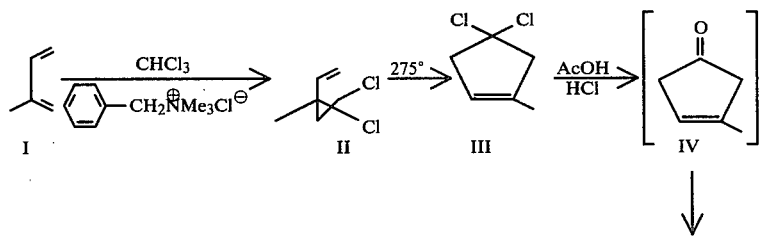

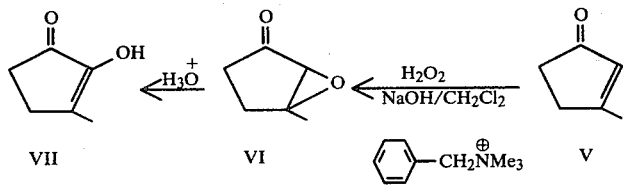

The above-noted synthesis consists of five separate steps.

1,1-Dichloro-2-methyl-2-vinylcyclopropane (II) was obtained by the selective addition of dichlorocarbene to the more highly substituted double bond of isoprene. The dichlorocarbenoid species which is preferred over other dihalocarbenoid species was generated in situ by decomposition of chloroform in a two-phase system with the use of 50% sodium hydroxide and a catalytic amount of a quaternary salt such as trimethylbenzylammonium chloride. Preparation of this compound in a two-phase system has not been reported (See "Compendium of Phase-Transfer Reactions and Related Synthetic Methods," Walter E. Keller, Editor, Fluka A. G., Switzerland, 1978, and references cited therein). Ketley et al., (J. Org. Chem. 31, 305 (1966)) reported the synthesis using potassium tert-butoxide in pentane with much lower yields. In this instant case, yield of 41 percent was obtained using 1:1 ratio of isoprene to chloroform whereas a 2:1 ratio afforded the product in 50 percent yield.

It is noted that U.S. Pat. No. 2,951,878 issued to Neureiter, teaches a similar compound, namely vaporized 1,1-dichloro-2-vinylcyclopropane, passed through a furnace at 425°–575° C. under vacuum produces a number of products, including 20–35% monochlorocyclopentadiene; 2–10% 4,4-dichlorocyclopentene; 20–40% 1,1-dichloropenta-1,3-diene and 1–4% dichloroisoprene. A later patent to the same inventor, U.S. Pat. No. 2,981,756, claims 4,4-dichlorocyclopentene using the identical reaction conditions.

The product of the above condensation (II) underwent thermal isomerization to give exclusively 1-methyl-4,4-dichlorocyclopentene (III). The pyrolysis was carried out by repeatedly passing II in a stream of nitrogen through a glass column packed with glass wool maintained at 275° C. The pyrolysate was collected in an ice-cooled flask and recycled. Theory yield of III exceeded 90% with 95% recovery. This method was superior to pyrolysis methods whereby II was passed through a column packed with either glass beads or hollow glass rods at 220°–230° C. In these latter cases, recovery was poor with 50 percent weight loss in the column.

One key step in the present synthesis is the hydrolysis of 1-methyl-4,4-dichlorocyclopentene (III) to 3-methyl-2-cyclopenten-1-one (V). Hydrolysis of gem-dichloro compounds to ketones normally requires rather drastic conditions, such as concentrated sulfuric acid. Surprisingly, it was found that III was readily hydrolyzed with a mixture of dilute hydrochloric acid and a small amount of glacial acetic acid to give the desired cyclopentenone V in excellent yield. The initially formed unconjugated ketone IV was isomerized to the more stable enone V. The ease with which the hydrolysis took place was presumably due to the presence of the double bond in III, since ionization to a bishomocyclopropenium ion VIII intermediate greatly lowered the energy of activation.

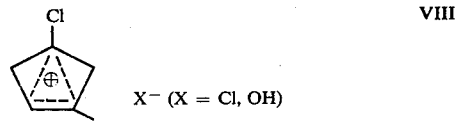

Distillation of the hydrolysis product yielded pure 3-methyl-2-cyclopenten-1-one V. Any unreacted III was recovered by distillation at this stage.

Although acid catalysis is usually preferred, it was found that the hydrolysis of 1-methyl-4,4-dichlorocyclopentene (III) could be accomplished using basic catalysis ($Na_2CO_3$/aq. ethanol) or aqueous metal ion catalysis ($Zn^{++}$, $Fe^{+++}$, $Cu^{++}$, $Hg^{++}$, $Ag^+$, etc.). In the basic hydrolysis, the reaction with $Na_2CO_3$ was very clean, but reaction with $Na_2S$ led to extremely low recovery. Interestingly, hydrolysis with heavy metal ion catalysis produced small amounts of isomers presumed to be 3-methyl-3-cyclopenten-1-one and 4-methyl-2-cyclopenten-1-one in addition to V. These isomers were readily isomerized to V with alumina. In the hydrolysis step reaction temperatures of about 50° to 100° C. are useful with reflux temperature of the reaction medium usually used for convenience.

Epoxidation of V with basic hydrogen peroxide in a two-phase system with a catalytic amount of phase transfer catalyst yielded 2,3-epoxy-3-methyl-cyclopentanone VI in 79% theory yield. Epoxide VI underwent decomposition in aqueous alkaline solution. By stirring in a two-phase system, the epoxidation product was not directly exposed to the alkaline solution during the course of the reaction. This epoxidation step with its high yield represents a considerable improvement over the literature yields of 40–53%.

Isomerization of the epoxy ketone VI with dilute mineral acid afforded th product VII, 2-hydroxy-3-methylcyclopent-2-en-1-one, in high yield. This step is well known in the literature. A novel process for this epoxide isomerization involves stirring with an ion exchange resin ($H^+$ form) in water at room temperature. Depending on the type of ion exchange resin, the time of reaction can be a critical factor in producing good yields.

The phase transfer catalyst used in the respective steps I→II and V→VI can advantageously be any of the effective phase transfer catalysts. Preferred catalysts include tertiaryamine quaternary salts represented by the formula $(R_1)_3N^+R_2X^-$ wherein $R_1$ is a lower alkyl group of from about 1–6 carbon atoms, $R_2$ can be an alkyl, aryl, or aralkyl group and X is halogen (Cl, Br). Quaternary ammonium salts prepared from trialkylamines and aralkyl halides such as benzylchloride are especially preferred because of the ease of preparation, cost and stability.

Product isolation was achieved by the usual physical techniques and product identification confirmed by NMR, infra-red spectra and gas chromatography.

The following examples, representatives of the invention, are not intended to limit the scope of the invention in any manner. All percentages are weight percentages and all temperatures are in degrees centigrade unless otherwise specified.

EXAMPLE 1

1,1-Dichloro-2-methyl-2-vinylcyclopropane

A mixture of 0.2 g of trimethylbenzylammonium chloride, 30 ml of 50% sodium hydroxide (0.625 mole) and 48 g (0.7 mole) of isoprene was shaken in a sealed glass bottle with a wrist shaker, while 40 g (0.34 mole) of chloroform was added dropwise by means of a syringe pump over a period of 40 minutes. The bottle was shaken at room temperature for 17 hours, was then opened and 100 ml of water was added. The organic layer was separated and the aqueous solution was extracted with methylene chloride. The combined organic solutions were dried ($Na_2SO_4$); filtered and distilled to give 25.63 g (50.3%) of 1,1-dichloro-2-methyl-2-vinylcyclopropane, bp 72°/65 mm Hg, as a colorless oil.

1Methyl-4,4-dichlorocyclopent-1-ene 1,1-Dichloro-2-methyl-2-vinylcyclopropane (26 g) was passed during 1.5 hours in a stream of nitrogen through a 1 —m Pyrex tube packed with glass wool and heated to 275° C. The product was collected in an ice-cooled flask and returned to the column. This procedure, repeated 10 times and monitored by GC, yielded 24.6 g (94.7%) of a slightly yellow liquid. GC indicated 91% purity of 1-methyl-4,4-dichlorocyclopentene. Table I shows the progress of the conversion with the number of passes:

TABLE I

| Ratio/No. of pass | 1 | 2 | 3 | 4 | 5 | 6 | 7 | 8 | 9 | 10 |
|---|---|---|---|---|---|---|---|---|---|---|
| Starting Material | 76 | 62 | 53 | 46 | 43 | 33 | 27 | 19 | 14 | 9 |
| Product | 24 | 38 | 47 | 54 | 57 | 67 | 73 | 81 | 86 | 91 |

EXAMPLE 2

The process of claim 1 was repeated using 24.19 g of 1,1-dichloro-2-methyl-2-vinylcyclopropane at a pyrolysis temperature of 275° C. After eleven passes, the conversion to 1-methyl-4,4-dichlorocyclopentene relative to starting material was 94:6. Distillation gave 21.02 g of colorless liquid (91% yield). Product purity by gas chromatographic analysis was 95%.

EXAMPLE 3

3-Methyl-2-cyclopenten-1-one 11.8 g of 1-methyl-4,4-dichlorocyclopentene (95% purity) was isomerized using 50 ml of 3% hydrochloric acid and 2.5 ml glacial acetic acid by heating under vigorous stirring in an oil bath for 4 hours. The reaction was monitored by thin layer chromatography or GC. The resulting tan colored reaction mixture was cooled and extracted with methylene chloride (2×100 ml). The combined methylene chloride extracts were washed with saturated sodium bicarbonate, water, brine, dried ($Na_2SO_4$), filtered and concentrated. The residue was distilled to yield 5.05 g (71%) of colorless oil bp. 98°/37 mm Hg. Only one major peak was detected in the gas chromatogram indicating a purity of greater than 99% for the product, 3-methyl-2-cyclopenten-1-one.

EXAMPLE 4

2,3-Epoxy-3-methylcyclopentanone

To a mixture of 0.521 g of trimethylbenzylammonium chloride, 10 ml $H_2O$, 19.22 g (0.2 mole) of 3-methyl-2-cyclopenten-1-one and 100 ml methylene chloride in a 500 ml three-necked flask equipped with a thermometer and a dropping funnel was added 23 ml (0.4 mole) of 50% hydrogen peroxide in one portion at 0°–5° C. 4 ml of 2.5 N sodium hydroxide solution was added dropwise over a period of 80 minutes. During the addition, the temperature of the reaction mixture was maintained at 5° C. The epoxidation was monitored by thin layer chromatography (silica gel 5 cm×10 cm, thickness 2 mm) $CH_2Cl_2$ : Ethyl Acetate/10:1 : $R_f$ product 0.51; $R_f$ starting material 0.30.

Figure 2:
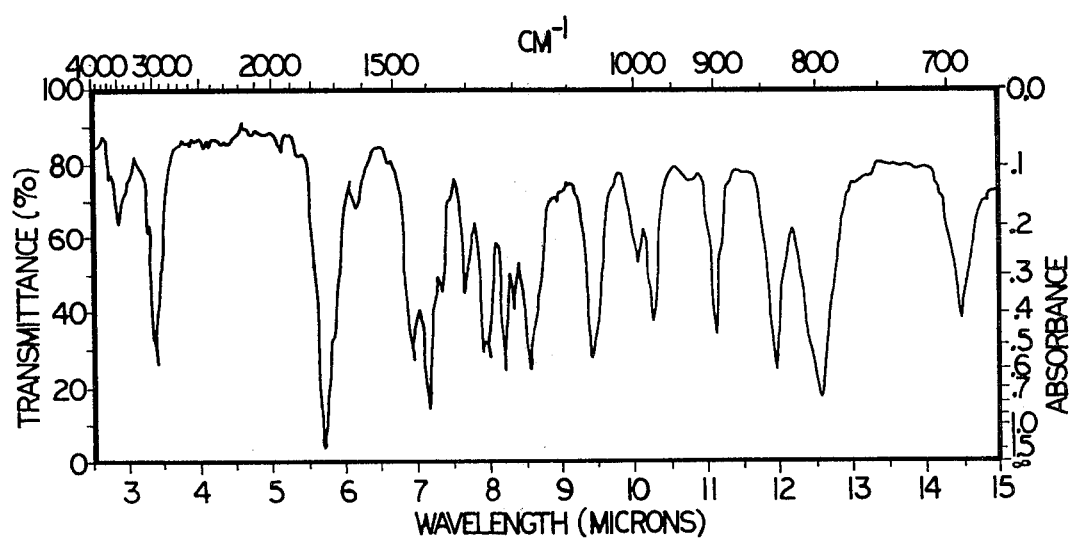

After stirring for 40 minutes at 5° C., thin layer chromatography indicated complete disappearance of starting material and the reaction mixture was poured into a separatory funnel. The methylene chloride layer was separated and the aqueous layer was extracted once with methylene chloride (100 ml). The combined methylene chloride solution was dried ($Na_2SO_4$), filtered and concentrated in a rotary evaporator (water bath temperature: 30° C.). The colorless residue was distilled to yield 17.71 g (79.06%) of a colorless liquid bp 65°/15 mm Hg. The gas chromatograph and infrared spectra of the product, 2,3-epoxy-3-methylcyclopentanone are shown as FIGS. 1 and 2 respectively.

EXAMPLE 5

2-Hydroxy-3-methylcyclopent-2-en-1-one

Isomerization of the epoxide of Example 4 was effected with ion exchange resin: 0.913 g of the epoxide was stirred vigorously with 16 ml of distilled water and 2 g of Dowex 50 WX16 ion exchange resin ($H^+$ form) at room temperature for 2 hrs. Thin layer chromatography (methylene chloride: ethyl acetate/10:1) indicated complete disappearance of starting epoxide. The reaction mixture was filtred, and the resins were washed with 10 ml methylene chloride which was then evaporated during suction filtration. The aqueous solution was concentrated to 7 ml. Upon cooling in an ice bath, 2-hydroxy-3-methylcyclopent-2-en-1-one was deposited which was collected as fine colorless needles weighting 734 mg (81%) mp 99°–101° C.

EXAMPLE 6

Isomerization of epoxide with dilute sulfuric acid

A mixture of 15 g of epoxide and 70 ml 0.2% sulfuric acid was heated with vigorus stirring in an oil bath maintained at 100° C. for 3 hrs. Upon cooling in an ice bath, white solid precipitated weighing 7.81 g, m.p. 95°–98°.

The aqueous filtrate was extracted once with pentane (100 ml) 0.19 g of yellow oil was obtained from the pentane extract. The aqueous solution was again extracted with ethyl acetate to give 1.71 g of yellow solid.

The yellow solids were combined and recrystallized in ethyl acetate to give 2.98 gm of white needles, m.p. 102°–103°. Lit. 102°–104°. Yield of product was 10.79 g (72%).

EXAMPLE 7

2-Hydroxy-3-ethylcyclopent-2-en-1-one

If the process of Example 1 is repeated using 2-ethyl-1,3-butadiene instead of isoprene1,1-dichloro-2-ethyl-2-vinylcyclopropane will result. If this is then subjected to the processes shown in Examples 3, 4, 5 and 6, the subject compound will be obtained.

EXAMPLE 8

Basic Hydrolysis of 4,4-dichloro-1-methylcyclopentene

A mixture of 4,4-dichloro-1-methylcyclopentene (1.51 g, 91% pure), sodium carbonate (2.0 g) in 50% aqueous ethanol (40 ml) was heated under reflux for 18.5 hr., cooled, and poured into water (20 ml). The product was extracted with methylene chloride (2×30 ml), which was, in turn, washed with water, brine, dried ($Na_2SO_4$) and evaporated to give an oil (0.8 g) which contained 88.7% of 3-methyl-2-cyclopentenone. Infrared and NMR spectra of the product are consistent with the structure. Calculated yield 83.5%.

What is claimed is:

1. Process for preparing alkyl cyclopentenolones having the structure

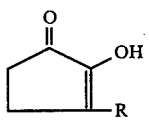

wherein R is a $C_{1-4}$ straight or branched chain lower alkyl radical which comprises:
 (a) reacting a 2-alkyl substituted butadiene with a dihalocarbenoid species to produce a 1,1-dihalo-2-alkyl-2-vinylcyclopropane.
 (b) passing the product of reaction (a) through a hot tube reactor at about 200°-350° C. to isomerize it to a 1-alkyl-4,4-dihalocyclopenten-1.
 (c) hydrolyzing a 1-alkyl-4,4-dihalocyclopent-1-ene to obtain a 3-alkyl-2-cyclopenten-1-one.
 (d) epoxidizing the product of reaction (c) to form 2,3-epoxy-3-alkylcyclopentan-1-one.
 (e) isomerizing said 2,3-epoxy-3-alkylcyclopentan-1-one under acid catalysis and isolating a 2-hydroxy-3-alkylcyclopent-2-en-1-one.

2. The process of claim 1 wherein the alkyl substituted butadiene is 2-methyl-1,3-butadiene and the cyclopentenolone product is 2-hydroxy-3-methylcyclopent-2-en-1-one.

3. The process of claim 1 wherein the alkyl substituted butadiene is 2-ethyl-1,3-butadiene and the cyclopentenolone product is 2-hydroxy-3-ethylcyclopent-2-en-1-one.

4. Process for preparing 2-hydroxy-3-methylcyclopent-2-en-1-one comprising:
 (a) reacting 2methyl-1,3-butadiene with a dichlorocarbenoid species in the presence of a catalytic amount of a quaternary ammonium salt to produce 1,1-dichloro-2-methyl-2-vinylcyclopropane.
 (b) passing the product of reaction (a) through a hot tube reactor at a temperature of about 200° C. to about 300° C. to isomerize it to 1-methyl-4,4-dichlorocyclopent-1-ene.
 (c) hydrolyzing 1-methyl-4,4-dichlorocyclopent-1-ene at temperatures from about 40°-100° C. in the presence of a catalyst selected from the group consisting of acid catalyst, base catalyst or aqueous metal ion catalyst to obtain 3-methyl-2-cyclopenten-1-one therefrom.
 (d) epoxidizing said 3-methyl-2-cyclopenten-1-one by reacting with hydrogen peroxide in a two-phase system containing a phase transfer catalyst to form 2,3-epoxy-3-methylcyclopentan-1-one.
 (e) isomerizing said 2,3-epoxy-3-methylcyclopentan-1-one under acid catalysis and isolating 2-hydroxy-3-methylcyclopent-2-en-1-one.

5. The process of claim 4 wherein two moles 2-methyl-1,3-butadiene is reacted with dichlorocarbene generated from one mole of chloroform: the 1,1-dichloro-2-methyl-2-vinylcyclopropane is isomerized by passage in an inert gas stream through a glass tube containing glass wool at about 250° C. to about 350° C. and the 1-methyl-4,4-dichlorocyclopropene formed is isomerized to 3-methyl-2-cyclopentene-1-one using a dilute mixture of hydrochloric acid and acetic acid.

6. The process of claim 5 wherein 3-methyl-2-cyclopenten-1-one is converted to the epoxide using trimethylbenzylammonium chloride as phase transfer catalyst.

7. The process of claim 4 wherein the hydrolysis of 1-methyl-4,4-dichlorocyclopent-1-ene is catalyzed with sodium carbonate.

8. A process for the conversion of 1-methyl-4,4-dihalocyclopent-1-ene to 2-hydroxy-3-methylcyclopent-2-en-1-one which comprises hydrolyzing 1-methyl-4,4-dihalocyclopent-1-ene in the presence of a dilute mixture of hydrochloric acid and glacial acetic acid at temperatures of 50°-100° C. and producing 3-methyl-2-cyclopenten-1-one therefrom; epoxidizing said 3-methyl-2-cyclopenten-1-one by reacting with basic hydrogen peroxide, in a two-phase system containing a phase transfer catalyst to produce 2,3-epoxy-3-methylcyclopentanone, isomerizing it to 2-hydroxy-3-methylcyclopent-2-en-1-one.

9. The process of claim 8 wherein the epoxidation is conducted in methylene chloride and the phase transfer catalyst is a quaternary ammonium salt.

* * * * *